US008961983B2

(12) United States Patent
Akiyoshi et al.

(10) Patent No.: US 8,961,983 B2
(45) Date of Patent: Feb. 24, 2015

(54) MUCOSAL VACCINE USING CATIONIC NANOGEL

(71) Applicant: National University Corporation Tokyo Medical and Dental University, Tokyo (JP)

(72) Inventors: Kazunari Akiyoshi, Tokyo (JP); Hiroshi Kiyono, Tokyo (JP); Yoshikazu Yuki, Tokyo (JP); Tomonori Nochi, Chapel Hill, NC (US)

(73) Assignee: National University Corporation Tokyo Medical and Dental University, Tokyo (JP)

( * ) Notice: Subject to any disclaimer, the term of this patent is extended or adjusted under 35 U.S.C. 154(b) by 0 days.

(21) Appl. No.: 14/478,127

(22) Filed: Sep. 5, 2014

(65) Prior Publication Data

US 2014/0370056 A1 Dec. 18, 2014

Related U.S. Application Data

(62) Division of application No. 13/126,357, filed as application No. PCT/JP2009/068647 on Oct. 30, 2009, now abandoned.

(30) Foreign Application Priority Data

Oct. 31, 2008 (JP) ................................. 2008-281065

(51) Int. Cl.
*A61K 39/00* (2006.01)
*A61K 39/02* (2006.01)
*A61K 39/12* (2006.01)
*A61K 39/385* (2006.01)
*A61K 47/00* (2006.01)
*A61K 39/08* (2006.01)

(52) U.S. Cl.
CPC ............ *A61K 39/08* (2013.01); *A61K 2039/541* (2013.01); *A61K 2039/6087* (2013.01)
USPC .................. 424/184.1; 424/193.1; 424/204.1; 424/234.1; 424/274.1; 424/278.1

(58) Field of Classification Search
None
See application file for complete search history.

(56) References Cited

U.S. PATENT DOCUMENTS

| 6,656,481 | B1 | 12/2003 | Shiku et al. |
| 2003/0219457 | A1 | 11/2003 | Williams |
| 2005/0163808 | A1 | 7/2005 | Blake et al. |
| 2010/0297187 | A1 | 11/2010 | Stoloff et al. |
| 2011/0206729 | A1 | 8/2011 | Akiyoshi et al. |

FOREIGN PATENT DOCUMENTS

| JP | 2007252304 A | 10/2007 |
| JP | 2008231343 A | 10/2008 |
| JP | 2008281065 A | 11/2008 |
| WO | WO-9809650 A1 | 3/1998 |

OTHER PUBLICATIONS

European Search Report Dated Jun. 7, 2013.
Tsuji et al., "Induction of Immune Response Against NY-ESO-1 by CHP-NY-ESO-1 Vaccination and Immune Regulation in a Melanoma Patient", Cancer Immunology Immunotherapy, 2008, vol. 57, No. 10, pp. 1429-1437.
Akiyoshi et al., "Self-Assembled Hydrogel Nanoparticle of Cholesterol-bearing Pullulan as a Carrier of Protein Drugs: complexation and Stabilization of Insulin", Journal of Controlled Release, vol. 54, No. 3, Aug. 14, 1998, pp. 313-320.
Kitano et al., "HER2-Specific T-Cell Immune Responses in Patients Vaccinated with Truncated HER2 Protein Complexed with Nanogels of Cholesteryl Pullulan", Clincial Cancer Research, 2006, vol. 12, No. 24, pp. 7397-7405.
Kageyama et al., "Humoral Immune Responses in Patients Vaccinated with 1-146 HER2 Protein Complexed with Cholesteryl Pullulan Nanogel", Cancer Science, 2008, vol. 99, No. 3, pp. 601-607.
Bacon et al., "Carbohydrate Biopolymers Enhanced Antibody Responses to Mucosally Delivered Vaccine Antigens", Infected and Immunity, 2000, vol. 68, No. 10, pp. 5764-5770.
Illum et al., "Chitosan as a Novel Nasal Delivery System for Vaccines", Advanced Drug Delivery Reviews, 2001, vol. 51, No. 1-03, pp. 81-96.
Des Rieux et al., "Nanoparticles as Potential Oral Delivery Systems of Proteins and Vaccines: A Mechanistic Approach", Journal of Controlled Release, 2006, vol. 116, No. 1, pp. 1-27.
Peek et al., "Nanotechnology in Vaccine Delivery", Advanced Drug Delivery Reviews, 2008, vol. 60, No. 8, pp. 915-926.
Towards Development of Nasal Vaccines—Current Status; Author: Yuichi Kurono, Inflammation & Immunity, 2001, vol. 9, No. 6, pp. 632-637. English translation of abstract.
Office Action dated May 7, 2013 of JP-2008281065-A; filed Nov. 20, 2008; Applicant NSK, Ltd.
Satoh et al. "Nanoparticle of Cholesterol-Bearing Pullulan as a Carrier of Anticancer Drugs", European Journal of Cnacer, Supplement, Pergamon, Oxford, GB, 2008, vol. 6, No. 9, pp. 139.
Soane et al., "Evaluation of the Cleamance Characteristics of Bioadhesive Systems in Humans", International Journal of Pharmaceutics, 1999, vol. 178, No. 1, pp. 55-65.
European Patent Office Communication; Application No. 09 823 688.8-1412; dated Jul. 7, 2014.
Tramont et al., "Progress in the Development of an HIV Vaccine", Expert Opinion, Emerging Drugs, 2003, vol. 8, No. 1, pp. 37-45.
Toita et al., "Protein-Conjugated Quantum Dots Effectively Delivered into Living Cells by a Cationic Nanogel", Journal of Nanoscience and Nanotechnology, 2008, vol. 8, pp. 2279-2285.
Office Action dated May 7, 2013 of JP-2008281065-A.

*Primary Examiner* — Albert Navarro
(74) *Attorney, Agent, or Firm* — McCarter & English

(57) ABSTRACT

A mucosal vaccine for the prevention or treatment of microbial infections is described that is capable of inducing vaccine antigen-specific immune responses in an organism without the addition of a mucosal adjuvant. The mucosal vaccine comprises a composite of a nanogel comprising a hydrophilic polysaccharide having a cationic functional group and a hydrophobic cholesterol added thereto as a side chain and a vaccine antigen. The vaccine is administered via a mucosal route.

7 Claims, 13 Drawing Sheets

MUCOSAL VACCINE USING CATIONIC NANOGEL

RELATED APPLICATIONS

This application is a division of U.S. patent application Ser. No. 13/126,357, filed Apr. 27, 2011, which is a national stage application filed under 35 U.S.C. §371 of PCT/JP2009/068647, filed Oct. 30, 2009, which is incorporated by reference herein in its entirety and which claims the benefit of Japanese Patent Application No. 2008-281065, filed Oct. 31, 2008, which is incorporated by reference herein in its entirety.

FIELD OF THE INVENTION

The present invention relates to a mucosal vaccine comprising a composite of a vaccine antigen and a cationic nanogel that is transnasally or orally administered.

BACKGROUND OF THE INVENTION

Non-injection mucosal vaccines are safe and convenient to use, and thus they have drawn attention as the next-generation vaccines. It was necessary to administer a mucosal vaccine simultaneously with a mucosal adjuvant in order to induce effective antigen-specific immune responses with the use of a mucosal vaccine. As mucosal adjuvants, toxin-related proteins, such as cholera toxins (CT) or detoxicated cholera toxins (mCT), are known. Addition of such mucosal adjuvants to mucosal vaccines enables transnasal vaccines to induce mucosal IgA in addition to antigen-specific systemic IgG. However, such mucosal adjuvant may disadvantageously migrate to the brain, and the safety thereof on organisms has remained problematic.

The present inventors developed nanogels comprising molecules such as cholesterol-bearing pullulan (CHP), which is composed of hydrophilic polysaccharides and hydrophobic cholesterol added thereto as a side chain, as DDS substrates (see WO 00/12564, JP Patent Publication (kokai) No. 2005-298644 A, WO 2006/049032, JP Patent Publication (kokai) No. 2006-143808 A, WO 2007/083643, JP Patent Publication (kokai) No. 2007-252304 A, and Hasegawa et al., *Saibou Kougaku* (Cell Technology), Vol. 26, No. 6, 2007, pp. 679-685). Specifically, CHP is capable of self-assembly in an aqueous environment, and it is converted into colloids (nanogels) with diameters of 20 to 30 nm capable of enclosing various substances therein. An excellent feature of CHP is the "molecular chaperone effects." That is, upon enclosure of a molecule, such as a protein molecule, inside CHP nanogels, followed by release thereof, refolding takes place at the time of release, a physiological 3-D structure is formed, and normal activity is exerted.

While the use of such nanogels for vaccine preparations has been reported (see JP Patent No. 4033497), such nanogels become usable upon activation of cytotoxic T cells (CTL) for anti-cancer, anti-virus, or autoimmune disease treatment applications. That is, it could not be said that nanogels can always exert the effects of mucosal vaccines.

Also, use of a liposome having a lipid membrane comprising glycolipids and phospholipids for the delivery of oral vaccines had been reported (see JP Patent Publication (kokai) No. H05-339169 A (1993)).

SUMMARY OF THE INVENTION

A mucosal vaccine for transnasal or oral administration, which is capable of inducing vaccine antigen-specific immune responses in organisms without the addition of a mucosal adjuvant such as a toxin-related protein, (e.g., cholera toxin (CT) or a detoxicated cholera toxin (mCT)), is provided.

Specific disclosed embodiments include the following:

[1] A mucosal vaccine preparation used for prevention or treatment of a microbial infection, comprising a composite of a nanogel, the nanogel comprising a hydrophilic polysaccharide having a cationic functional group with a hydrophobic cholesterol added thereto as a side chain and a vaccine antigen, wherein the vaccine preparation is administered via the mucosal route.

[2] The mucosal vaccine preparation according to [1], wherein the cationic functional group is an amino group.

[3] The mucosal vaccine preparation according to [1], wherein the nanogel is cholesterol-bearing pullulan.

[4] The mucosal vaccine preparation according [1], wherein the vaccine antigen is derived from a microorganism.

[5] The mucosal vaccine preparation according to [4], wherein the microorganism is selected from the group consisting of a virus, a bacterium, a protozoan, and a fungus.

[6] The mucosal vaccine preparation according to [5], wherein the vaccine antigen is selected from the group consisting of a C-terminal avirulent region of the heavy chain of botulinus toxin, tetanus toxoid, and the AIDS virus membrane antigen molecule (gag p24).

[7] The mucosal vaccine preparation according to [1], wherein the vaccine antigen is combined with the nanogel at a molar ratio of 1:1 to 1:10.

[8] The mucosal vaccine preparation according to [1], wherein the vaccine preparation is a nasal preparation.

[9] The mucosal vaccine preparation according to [1], wherein the vaccine preparation is an oral preparation.

[10] A method for producing the mucosal vaccine preparation of claim 1 comprising mixing a nanogel comprising a hydrophilic polysaccharide having a cationic functional group with hydrophobic cholesterol added thereto as a side chain and a vaccine antigen at about 4° C. to about 37° C. for about 2 to about 48 hours.

[11] The method for producing a mucosal vaccine preparation according to [10], wherein the cationic functional group is an amino group.

[12] The method for producing a mucosal vaccine preparation according to [10], wherein the nanogel is cholesterol-bearing pullulan.

[13] The method for producing a mucosal vaccine preparation according to [10], wherein the vaccine antigen is derived from a microorganism.

[14] The method for producing a mucosal vaccine preparation according to [13], wherein the microorganism is selected from the group consisting of a virus, a bacterium, a protozoan, and a fungus.

BRIEF DESCRIPTION OF THE DRAWINGS

FIG. 2 shows the IgG1, IgG2a, IgG2b, and IgG3 antibody titers to Hc in the serum of a transnasally immunized mouse. The four aligned bar graphs each show IgG1, IgG2a, IgG2b, and IgG3 from the left.

FIG. 11 shows the total IgG antibody titer to botulinus toxin in the serum of a mouse transnasally immunized with cationic nanogels or cationic liposomes.

DETAILED DESCRIPTION OF THE INVENTION

Figure 1:
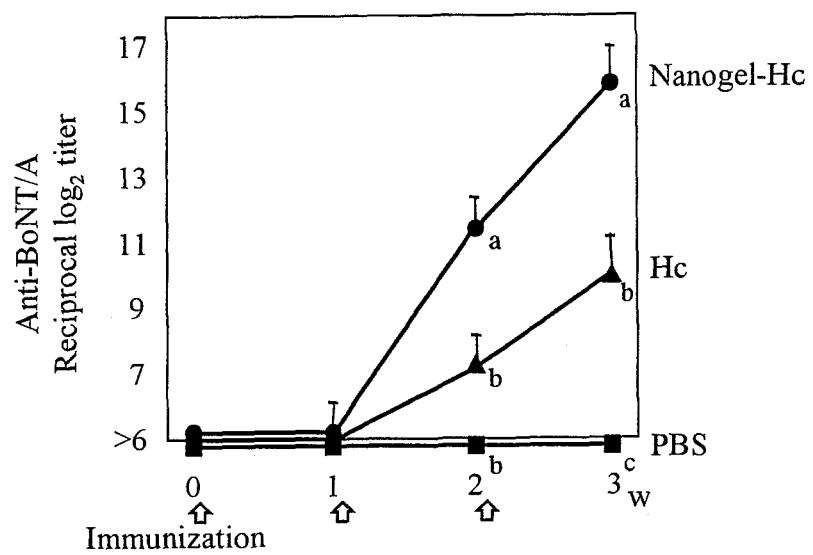
FIG. 1 shows the total IgG antibody titer to Hc in the serum of a transnasally immunized mouse.

The present inventors previously developed a nanogel comprising a hydrophilic polysaccharide with hydrophobic cholesterol added to the hydrophilic polysaccharide as a side chain, which can be used for the delivery of a substance such as a physiologically active protein.

The present inventors conducted concentrated studies in order to examine the applicability of such nanogel to the production of mucosal vaccines. As a result, they discovered that administration of a composite of nanogels comprising cationic functional groups such as amino groups and vaccine antigens (i.e., viral or bacterial proteins) through the mucous membrane of the nasal cavity or the mucous membrane of the intestinal canal would induce systemic immune responses and mucosal immune responses more effectively than would be possible with the use of a liposome, and such administration would be useful for prevention or treatment of viral or bacterial infections. This has led to the completion of the present invention.

The disclosed mucosal vaccine preparation prepared by combining a vaccine antigen and a cationic nanogel effectively induces systemic and mucosal immune responses in an animal via transmucosal administration, such as transnasal or oral administration. The disclosed mucosal vaccine involves the use of cationic nanogels. Accordingly, vaccine antigens can be efficiently delivered to the immune system, and immune responses are induced more effectively than a case in which non-cationic nanogels or cationic liposomes are used. The disclosed mucosal vaccine can be effectively used for prevention or treatment of viral or bacterial infections of an animal.

Herein the term "nanogel" refers to a hydrophobized polymer gel nanoparticle comprising a hydrophilic polysaccharide with hydrophobic cholesterol added thereto as a side chain. Nanogels can be produced by the method described in, for example, WO 00/12564 (the title of the invention: High-purity polysaccharide containing hydrophobic groups and process for producing the same).

At the outset, a hydroxyl-group-containing hydrocarbon or sterol having 12 to 50 carbon atoms is allowed to react with a diisocyanate compound represented by the formula OCN-R1-NCO, wherein R1 represents a hydrocarbon group having 1 to 50 carbon atoms, to produce an isocyanate-group-containing hydrophobic compound that had reacted with a molecule of a hydroxyl-group-containing hydrocarbon or sterol having 12 to 50 carbon atoms. Subsequently, the resulting isocyanate-group-containing hydrophobic compound is subjected to a further reaction with a polysaccharide to produce a polysaccharide containing a hydrophobic group comprising a hydrocarbon or steryl group having 12 to 50 carbon atoms as a hydrophobic group. The reaction product may be purified using a ketone-based solvent to produce a high-purity hydrophobic-group-containing polysaccharide. Examples of polysaccharides include pullulan, amylopectin, amylose, dextran, hydroxyethyl dextran, mannan, levan, inulin, chitin, chitosan, xyloglucan, and water-soluble cellulose.

Examples of nanogels that are preferably used in the present invention include cholesterol-bearing pullulan (hereafter referred to as "CHP") and a CHP derivative. In CHP, 1 to 10 and preferably 1 to several cholesterol molecules are substituted with pullulan having a molecular weight of 30,000 to 200,000 (e.g., 100,000) per 100 monosaccharide units. CHP properties can be modified in terms of the amount of cholesterol substitution depending on protein size or degree of hydrophobicity. In order to control the hydrophobic properties of CHP, an alkyl group having 10 to 30 and preferably about 12 to 20 carbon atoms may be introduced. The nanogels used in the present invention have a particle diameter of 10 to 40 nm and preferably 20 to 30 nm. Nanogels are extensively commercialized, and such commercialized nanogels can be used in the present invention.

The disclosed mucosal vaccine involves the use of nanogels into which positively charged functional groups, such as amino groups, have been introduced. The number of amino groups introduced into nanogels is 1 to 50 and preferably 5 to 30 per 100 glucose monosaccharides of CHP. A preferable example of a method for introducing amino groups into nanogels is a method involving the use of amino-group-added cholesterol pullulan (CHPNH$_2$) described below.

CHP dried under reduced pressure (0.15 g) is dissolved in 15 ml of a dimethyl sulfoxide (DMSO) solvent, 75 mg of 1-1'-carbonyldiimidazole is added thereto under a nitrogen stream, and the reaction is allowed to proceed at room temperature for 4 hours. Ethylenediamine (300 mg) is slowly added to the reaction solution, and the resultant is agitated for 24 hours. The reaction solution is dialyzed against distilled water for 6 days. The resultant is lyophilized to obtain an opalescent solid. The degree of substitution of ethylenediamine is determined via elemental analysis or H-NMR analysis. The number of substituents to be introduced can be changed as necessary. By changing the number of substituents introduced, the magnitude of the positive charge can be regulated, and the efficiency for vaccine antigen delivery from the vaccine antigen/cationic nanogel composite can be regulated.

The mucosal vaccine preparation of the present invention can efficiently induce vaccine antigen-specific systemic and mucosal immune responses in animals without the addition of another mucosal adjuvant.

Examples of vaccine antigens used for the mucosal vaccine of the present invention include antigens of microorganisms, such as bacteria, viruses, fungi, and protozoans, that cause infections in animals. Such antigens induce antigen-specific immune responses in animals, they can be used for vaccines, and they are thus referred to as "vaccine antigens."

Specific examples of microbial antigens include protein antigens of the following microorganisms: pathogenic viruses, such as influenza virus A, influenza virus B, hepatitis C virus, hepatitis A virus, hepatitis B virus, rotavirus, cytomegalovirus, respiratory syncytial (RS) virus, adenovirus, HIV, varicella-zoster virus, herpes simplex virus type 1 and type 2, ATL (adult T-cell leukemia) virus, coxsackie virus, enterovirus, exanthema subitum virus (HHV-6), measles virus, rubella virus, mumps (epidemic parotiditis) virus, poliovirus, Japanese encephalitis virus, rabies virus, hepatitis C virus, Norwalk virus (norovirus), rabies virus, respiratory syncytial (RS) virus, cytomegalovirus, foot and mouth disease virus, transmissible gastroenteritis virus, rubella virus, ATL virus, adenovirus, ECHO virus, herpes virus, smallpox virus, dengue fever virus, yellow fever virus, West Nile virus, SARS (coronavirus), ebola hemorrhagic fever virus (phyllovirus), Marburg virus (phyllovirus), Lassa fever virus, hantavirus, and Nipah virus; pathogenic bacteria, such as enteropathogenic *Escherichia coli* (e.g., enterohemorrhagic *E. coli*), Staphylococcus (e.g., *Staphylococcus aureus*), meningococci, *Pseudomonas aeruginosa, Streptococcus mutans, Vibrio cholera, Bacillus typhosus*, Chlamydia, Shigella, Pneumococcus, *Bordetella pertussis, Corynebacterium diphtheriae, Clostridium tetani, Haemophilus influenzae, Yersinia pestis, Clostridium botulinum, Bacillus anthracis, Francisella tularensis*, Salmonella, VRE (Enterococcus), *Mycobacterium tuberculosis*, Shigella, *Salmonella typhi, Salmonella paratyphi*, Chlamydia, amoebic dysentery, *Legionella*, Lyme Disease Borrelia, and Brucellosis (undulant fever); Rickettsia, such as Q fever rickettsia and Chlamydia; protozoans, such as causal agents of malaria and Cryptosporidium; and fungi, such as Cryptococcosis and Aspergillus. Examples of proteins derived from pathogenic microorganisms include proteins or peptides constituting pathogenic microorganisms (e.g., surface proteins, capsid proteins, and ciliary proteins), proteins or peptides produced by pathogenic microorganisms (e.g., toxins, enzymes, hormones, immunomodulating substances, receptors, and ligands thereof), and fragments or domains thereof. Protein antigens capable of inducing the production of antibodies that can attack and neutralize the aforementioned microorganisms may be used. A protein antigen to be used is not limited to only one type, and the mucosal vaccine of the present invention may contain a plurality of types of vaccine antigens derived from homologous or heterologous microorganisms. In the case of the influenza virus, for example, either or both the hemagglutinin (HA) receptor and the neuraminidase (NA) receptor may be combined with a cationic nanogel to produce a mucosal vaccine. Vaccine antigens can be obtained from microorganisms via processing, purification, or other means. Also, vaccine antigens can be chemically synthesized or can be obtained in the form of recombinant proteins via genetic engineering. The molecular weight of vaccine antigens contained in the mucosal vaccine preparation of the present invention is not limited. For example, it is approximately 500 to 1,000,000, and preferably approximately 1,000 to 200,000.

The vaccine antigen/cationic nanogel composite can be prepared by causing interactions between the cationic nanogels and the vaccine antigens so as to incorporate the vaccine antigens into the cationic nanogels. Preparation of a composite is referred to as "composite formation." The mixing ratio of vaccine antigens to cationic nanogels can be adequately determined in accordance with types of vaccine antigens and cationic nanogels used. For example, $CHPNH_2$ can be mixed with vaccine antigens at a molar ratio of 1:1 to 1:100, and preferably 1:1 to 1:10.

A vaccine antigen/cationic nanogel composite can be prepared by, for example, mixing vaccine antigens with cationic nanogels in a buffer and allowing the mixture to stand at 4° C. to 37° C. for 2 to 48 hours, and preferably 20 to 30 hours. A buffer used for preparation of a vaccine antigen/cationic nanogel composite can be adequately prepared in accordance with protein and nanogel types. An example is Tris-HCl buffer (50 mM, pH 7.6). The resulting vaccine antigen/nanogel composite can be analyzed in accordance with a conventional technique, such as gel permeation chromatography (GPC), atomic force microscopy (AFM), fluorescence microscopy, or confocal fluorescence microscopy.

The mucosal vaccine preparation of the present invention is administered via a mucosal route. Transmucosal administration is preferably carried out through the mucous membrane of the nasal cavity or the mucous membrane of the intestinal canal. In the former case, the vaccine preparation is administered transnasally. In the latter case, the vaccine preparation is administered orally. Nasal vaccine preparations induce immune responses in the nasal cavity via transnasal administration. Specifically, such vaccine preparations are capable of inducing local immune responses on the mucosal membrane of the respiratory tract (the upper respiratory tract, in particular), which is the route of microbial infection that causes viral or other infections. Nasal vaccine preparations may be administered into the nasal cavity via, for example, spraying, coating, or dropping. Oral vaccine preparations induce immune responses in the intestinal tract via oral administration. Mucosal vaccine preparations remain in the mucosal membrane, nasal-associated lymphoid tissue (NALT), or gut-associated lymphatic tissue (GALT) and releases vaccine antigens. Both nasal vaccine preparations and oral vaccine preparations induce systemic immune responses, produce virus-specific IgG or the like in organisms, induce mucosal immune responses, produce IgA antibodies in the mucosal membrane, and block infections via systemic and mucosal immune mechanisms. Thus, infections can be treated.

The mucosal vaccine preparation may contain known pharmaceutically acceptable stabilizers, antiseptics, antioxidants, and the like. Examples of stabilizers include gelatin, dextran, and sorbitol. Examples of antiseptics include thimerosal and β-propiolactone. An example of an antioxidant is α-tocopherol.

The mucosal vaccine preparation of the present invention can be administered to, for example, mammalians, such as humans, monkeys, mice, rats, rabbits, cats, cattles, dogs, horses, and goats, and birds, such as chickens.

A dose of the mucosal vaccine preparation can be adequately determined based on immunogen type, age or body weight of a subject, and other conditions. The mucosal vaccine preparation contains pharmaceutically effective amounts of vaccine antigens. The term "pharmaceutically effective amount(s)" refers to an amount of an antigen that is necessary for inducing immune responses to a vaccine antigen. For example, a dose of several μg to several ten mg of a vaccine antigen may be administered once to several times per day, and administration may take place several times at intervals of 1 to several weeks (e.g., administration may take place 1 to 5 times).

EXAMPLES

Embodiments of the present invention are described in detail with reference to the following examples, although the technical scope of the present invention is not limited to these examples.

Example 1

Preparation of Mucosal Vaccine

Cationic nanogels (cationic CHP) in which the degree of cholesterol substitution was 1.4 and the degree of ethylenediamine substitution was 18 per 100 monosaccharides were used (CHPNH$_2$ nanogels). A CHP derivative or cationic Pullulan was dissolved in a 1 mg/ml phosphate buffer solution (PBS). The CHPNH$_2$ nanogels were subjected to sonication for 15 minutes and then filtered through a 0.22-mm filter.

The C-terminal avirulent region of a heavy chain of botulinus toxin (Hc; molecular weight: 45,000), tetanus toxoid (TT; molecular weight: 150,000), or the AIDS virus membrane antigen molecule (gag p24; molecular weight: 24,000) expressed in E. coli and purified was mixed with the equimolar amount of cationic nanogels prepared in the manner described above, and the resulting mixture was subjected to reaction at 45° C. for 5 hours to prepare a composite. The obtained antigen/cationic nanogel composite was used as a mucosal vaccine using cationic nanogels. The gene of the purified C-terminal avirulent region of the heavy chain of botulinus toxin was inserted into a GST fusion protein expression vector (pGEX-6P3, GE Healthcare), transformed into E. coli Rossetta 2 (Novagen), and induced to express with the addition of 0.1 mM IPTG. Hc was centrifuged after ultrasonic disintegration of cells suspended in PBS, the resulting supernatant was purified via anion exchange chromatography (DEAE SEPHAROSE®; GE Healthcare), affinity chromatography (Glutathione SEPHAROSE®; GE Healthcare), or gel permeation chromatography (SEPHACRYL® S-100; GE Healthcare). GST fused to the N terminus of Hc was subjected to affinity chromatography and then removed via ablation with the addition of PRESCISSION® Protease (GE Healthcare) to the column. Tetanus toxoid was obtained from the Research Foundation for Microbial Diseases of Osaka University and gag p24 was obtained from Kyoko Yokota of the Department of Immunology at the National Institute of Infectious Diseases.

Example 2

Transnasal Immunization

The mucosal vaccine using cationic nanogels prepared in Example 1 or the antigen alone was administered to 6- to 8-week-old Balb/c mice (female) through the nasal cavity in an amount of 10 µg of Hc (88.9 µg of nanogel), 30 µg of TT (80.0 µg of nanogel), or 10 µg of gag p24 (166.7 mg of nanogel) per mouse once a week (3 times in total) to immunize mice transnasally. The amount of antigens administered (i.e., the amount of the solution) was adjusted to 15 µl in every experimental group, and 7.5 µl of the solution was administered to each nostril. PBS was administered as a control.

The blood was sampled before immunization and a week after immunization, and IgG antibody titers to botulinus toxin, TT, or gag p24 in the blood serum were measured to evaluate the systemic immune responses. The nasal cavity was washed with 200 µl of PBS a week after the final immunization, and the IgA antibody titer in the nasal wash solution was measured to evaluate immune responses in the mucosal system. The antibody titer was evaluated via ELISA.

Regarding serum IgG, antibody titers of IgG1, IgG2a, IgG2b, and IgG3 subclasses were measured, and antibody production pattern at the subclass level was evaluated in order to predict the Th1/Th2 immune balance after immunization. Further, the number of antigen-specific IgA-producing cells (blood plasma cells) in the nasal tissue a week after the final immunization was evaluated via ELISPOT.

Figure 2:
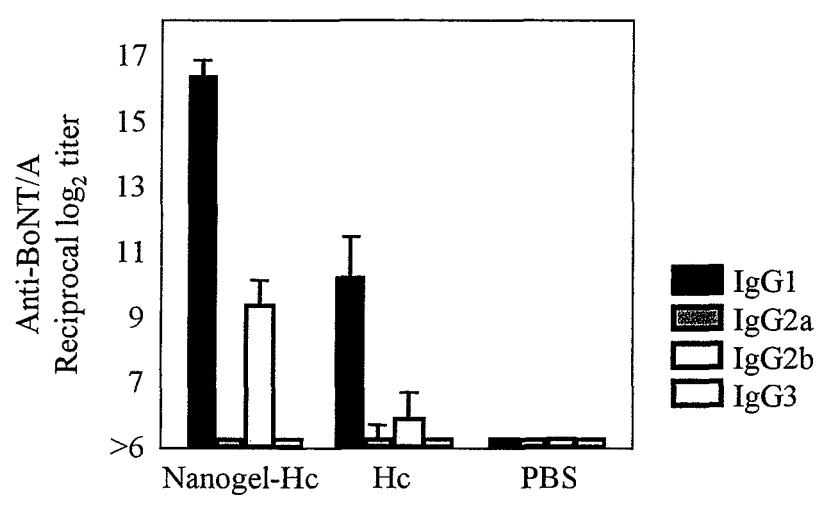

FIG. 1 shows the total IgG antibody titer to botulinus toxin in the serum. FIG. 2 shows the IgG1, IgG2a, IgG2b, and IgG3 antibody titers to botulinus toxin in the serum sampled after 3 immunization procedures. Further, FIG. 3 shows the total IgG antibody titer to TT in the serum, FIG. 4 shows the IgG1, IgG2a, IgG2b, and IgG3 antibody titers to TT in the serum sampled after 3 immunization procedures, and FIG. 5 shows the gag p24-specific IgG antibody titer after 3 immunization procedures.

Figure 6:
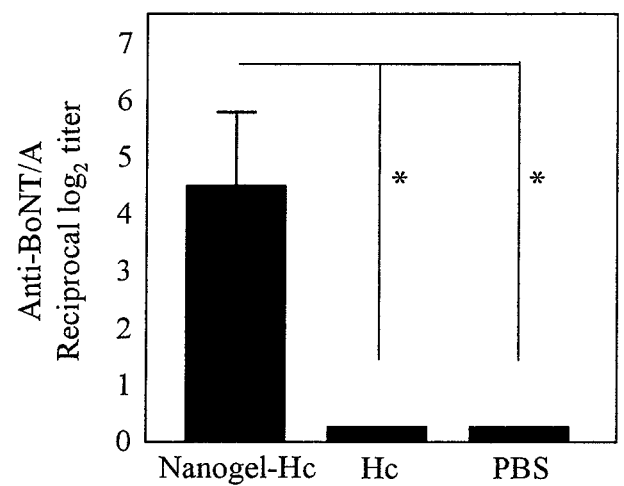
FIG. 6 shows the IgA antibody titer to Hc in the nasal wash solution used for a transnasally immunized mouse.
Figure 7:
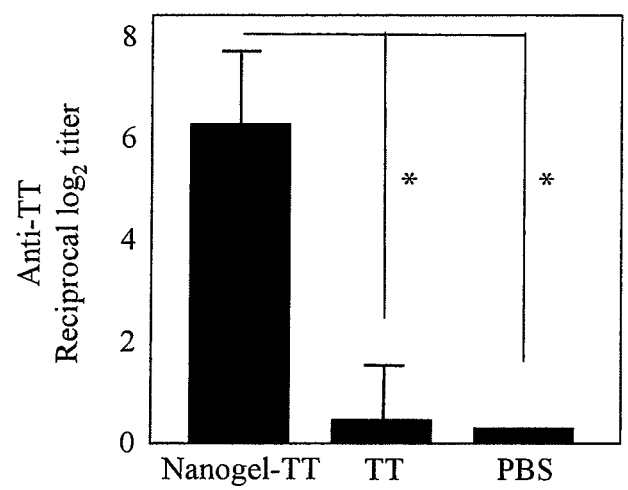
FIG. 7 shows the IgA antibody titer to TT in the nasal wash solution used for a transnasally immunized mouse.

FIG. 6 shows the IgA antibody titer to botulinus toxin in the nasal wash solution after 3 immunization procedures, and FIG. 7 shows the IgA antibody titer to TT in the nasal wash solution after 3 immunization procedures.

Figure 3:
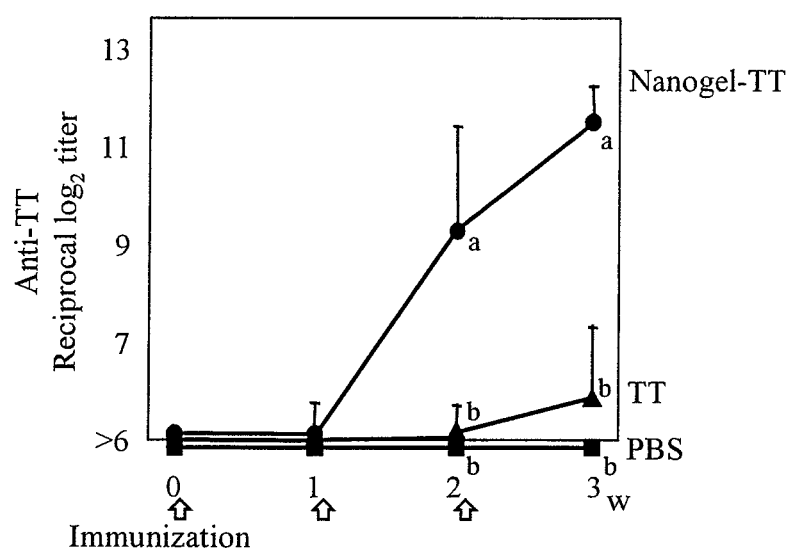
FIG. 3 shows the total IgG antibody titer to TT in the serum of a transnasally immunized mouse.
Figure 4:
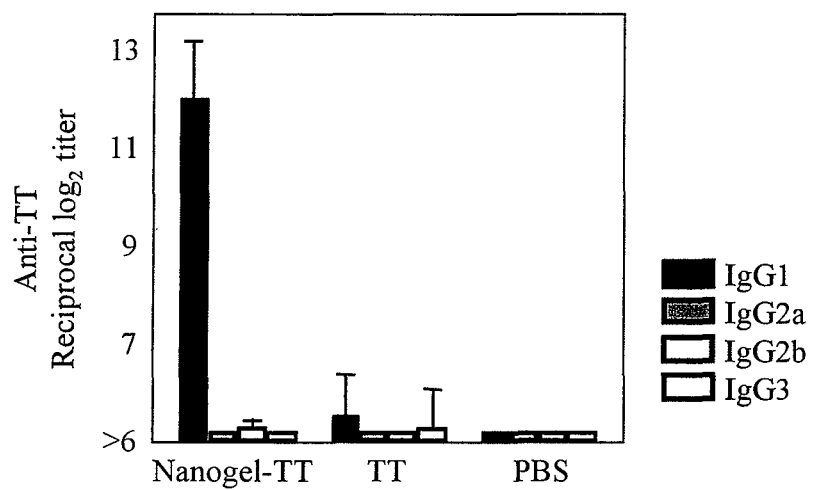
FIG. 4 shows the IgG1, IgG2a, IgG2b, and IgG3 antibody titers to TT in the serum of a transnasally immunized mouse. The four aligned bar graphs each show IgG1, IgG2a, IgG2b, and IgG3 from the left.
Figure 5:
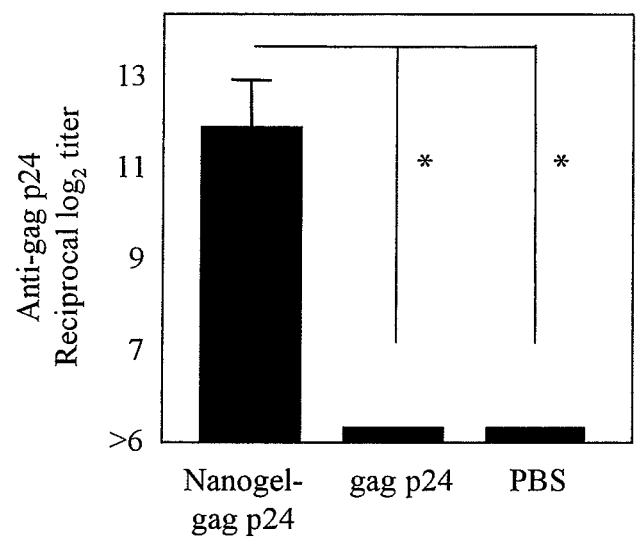
FIG. 5 shows the total IgG antibody titer to gag p24 in the serum of a transnasally immunized mouse.

As shown in FIGS. 1, 3, and 5, the total IgG antibody titers to botulinus toxin, TT, or gag p24 were significantly higher when the composite of Hc, TT, or gag p24 and cationic nanogels was administered, compared with the case when Hc, TT, or gag p24 was administered alone. This indicates that more potent systemic immune responses would be induced when the composite of Hc, TT, or gag p24 and cationic nanogels was administered, compared with the case when Hc, TT, or gag p24 was administered alone. As shown in FIGS. 2 and 4, also, a majority of antigen-specific IgG antibodies were of the IgG1 subclass, and the IgG2a level was significantly low. Thus, it was deduced that transnasal administration of a vaccine antigen/cationic nanogel composite would effectively induce Th2-type humoral immunity responses.

As shown in FIGS. 6 and 7, substantially no IgA antibody titer was recognized when Hc or TT was administered alone. When a composite of Hc or TT and cationic nanogels was administered, however, a high IgA antibody titer to botulinus toxin or TT was observed. This indicates that mucosal immune responses would be induced in the nasal mucous membrane only via transnasal administration of the mucosal vaccine of the present invention in the form of an antigen/cationic nanogel composite.

Figure 8:
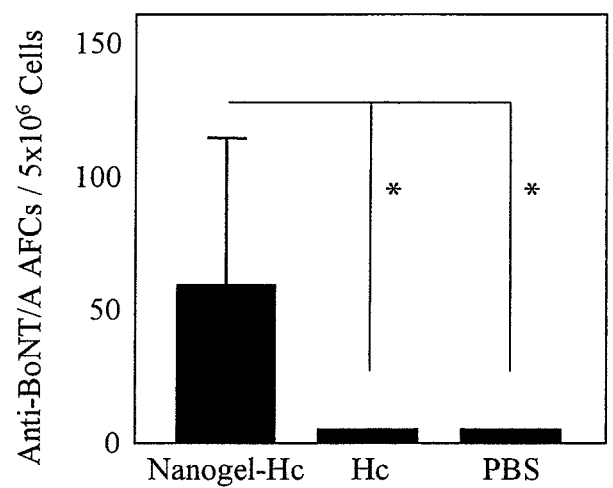
FIG. 8 shows the number of Hc antigen-specific IgA-producing cells in the nasal wash solution used for a transnasally immunized mouse.

FIG. 8 shows a comparison of the number of botulinus toxin antigen-specific IgA-producing cells in the mucous membrane of the nasal cavity. As shown in FIG. 8, no IgA-producing cells were produced when Hc was administered alone; however, IgA-producing cells were produced when a Hc/cationic nanogel composite was administered.

Example 3

Neutralization Effects after Transnasal Immunization Using Mucosal Vaccine Using Nanogels The vaccine using cationic nanogels using a C-terminal avirulent region of the heavy chain of botulinus toxin (Hc; molecular weight: 45,000) as the antigen prepared in Example 1 or Hc alone was administered transnasally to 5 mice for immunization in the same manner as in Example 2. PBS was administered as a negative control. After the mice were subjected to immunization 3 times, botulinus toxin (obtained from Professor Shunji Kozaki, Division of Veterinary Science, School of Life and Environmental Sciences, Osaka Prefecture University) was administered intraperitoneally in an amount 25,000 times greater than the lethal dose thereof via intraperitoneal administration (i.e., 500 ng) to analyze the survival effects. For the purpose of analyzing the neutralization effects of Hc-specific IgA induced in the nasal tissue, 10 µg of botulinum progenitor toxins (obtained from Wako Pure Chemical Industries, Ltd.) was administered transnasally and the later survival effects were also analyzed.

Figure 9:
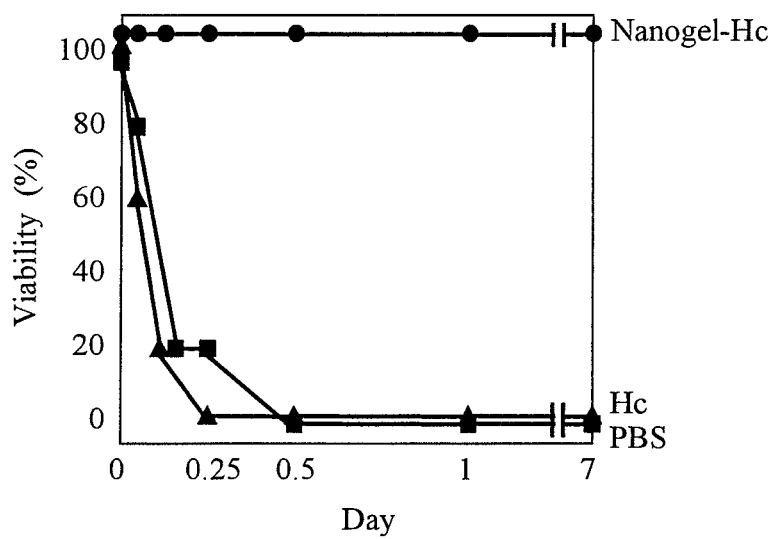
FIG. 9 shows the viability of a mouse transnasally immunized with Hc after intraperitoneal administration of botulinum toxins with the elapse of time.

FIG. 9 shows the viability of a mouse after intraperitoneal administration of botulinum toxin with the elapse of time. As shown in FIG. 9, all mice that had been immunized with Hc alone died within a day; however, all mice that had been immunized with an Hc/cationic nanogel composite remained alive 1 week later. This indicates that potent systemic neutralization and immunization would be induced via transnasal administration of the Hc/cationic nanogel composite.

Figure 10:
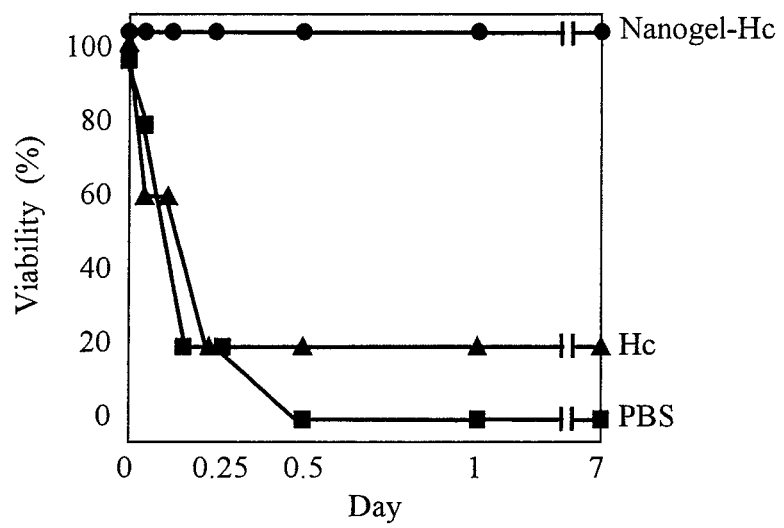
FIG. 10 shows the viability of a mouse transnasally immunized with Hc after transnasal administration of botulinum progenitor toxins with the elapse of time.

FIG. 10 shows the viability after transnasal administration of botulinum progenitor toxin with the elapse of time. As shown in FIG. 10, all mice that had been immunized with Hc alone died within a day; however, all mice that had been immunized with an Hc/cationic nanogel composite remained alive 1 week later. This indicates that botulinus toxin-specific mucosal IgA induced via transnasal administration of an Hc/cationic nanogel composite would effectively block mucosal infection by botulinum.

Example 4

Effects of Vaccine Using Cationic Nanogel for Immunity Induction in Comparison with Vaccine Using Cationic Liposome The vaccine using cationic nanogels using a C-terminal avirulent region of the heavy chain of botulinus toxin (Hc; molecular weight: 45,000) as the antigen prepared in Example 1 or the cationic liposome comprising the same amounts of the antigens of the same type (Project) was administered transnasally to 5 mice for immunization in the same manner as in Example 2. Project was obtained from PIERCE.

Figure 11:
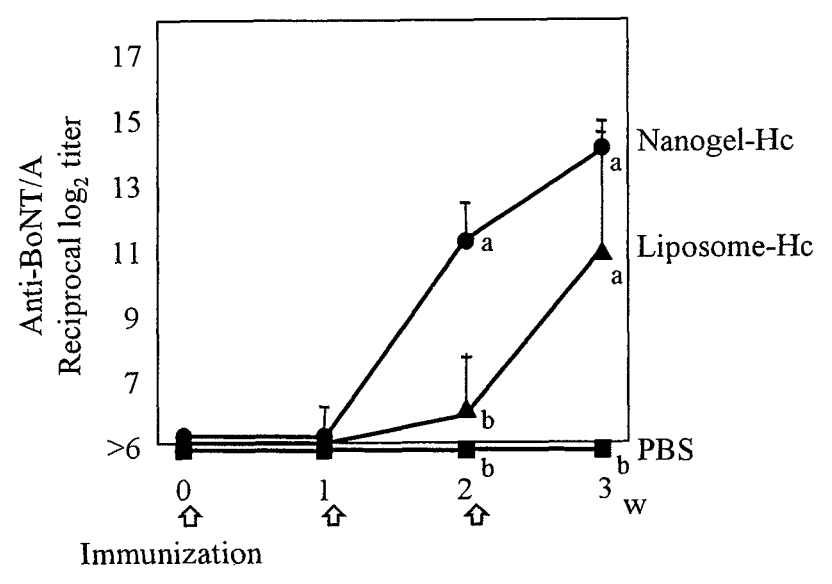

FIG. 11 shows the total IgG antibody titer to botulinus toxin after 3 immunization procedures.

As shown in FIG. 11, the total IgG antibody titer to botulinus toxin was significantly higher when the Hc/cationic nanogel composite was administered, compared with the case when Hc was administered in the form of an Hc/cationic liposome.

Figure 12:
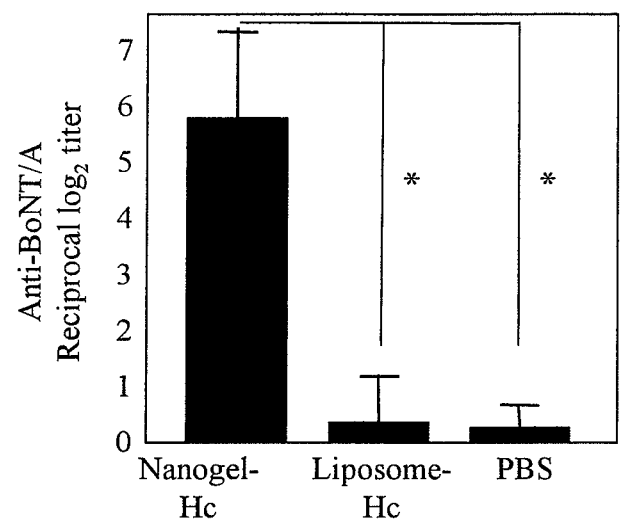
FIG. 12 shows the IgA antibody titer to gag p24 in the nasal wash solution used for a mouse transnasally immunized with cationic nanogels or cationic liposomes.

FIG. 12 shows the total IgA antibody titer to botulinus toxin after 3 immunization procedures.

As shown in FIG. 12, the total IgA antibody titer to botulinus toxin was significantly higher when the Hc/cationic nanogel composite was administered, compared with the case when Hc was administered in the form of a Hc/cationic liposome.

Example 5

Effects of Vaccine Using Cationic Nanogels for Retaining Antigen in Nasal Tissue and Migration to Cerebral Nervous System The C-terminal avirulent region of the heavy chain of botulinus toxin (Hc; molecular weight: 45,000) was labeled with 111In (indium) in accordance with a known technique with the use of DTPA anhydride. Labelling efficiency was 728.3233±115.3543 CPM/ng. Thereafter, the labelled Hc was combined with nanogels. The mucosal vaccine using nanogels combined with the labelled Hc (1,000,000 CPM) or the labeled Hc alone was administered transnasally to mice. The disposition thereafter in the brain, the olfactory bulb, the nasal cavity, the nasal-associated lymphoid tissue (NALT), the cervical lymph node, and the spleen was subjected to follow-up evaluation using a gamma counter. Specifically, the brain, the olfactory bulb, the nasal cavity, the nasal-associated lymphoid tissue (NALT), the cervical lymph node, and the spleen were extracted from mice 0.17, 1, 6, 12, 24, and 48 hours after transnasal administration, the samples were weighed, and gamma rays emitted by the samples were measured using a gamma counter.

Figure 13:
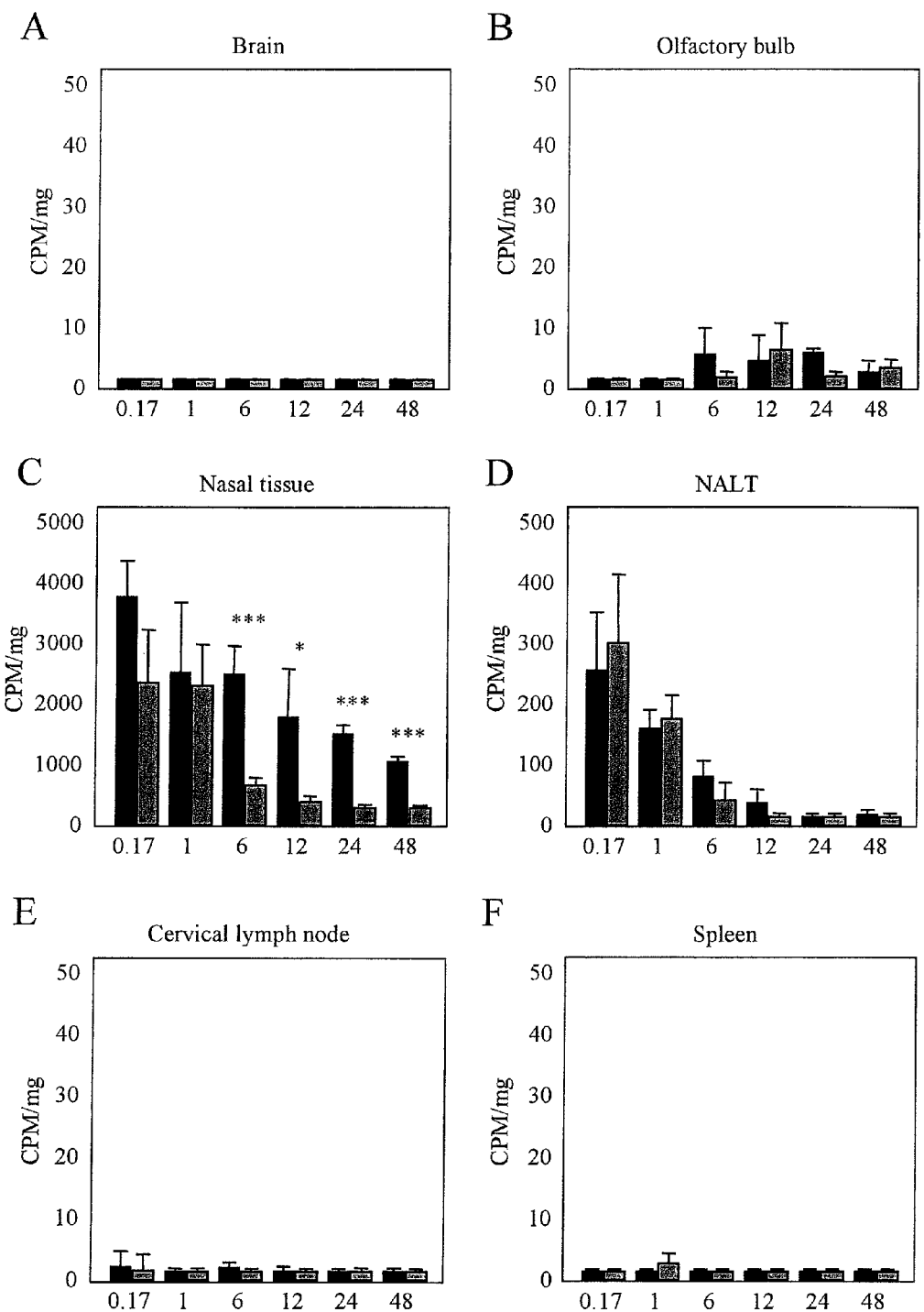
FIG. 13 shows the effects of cationic nanogel-based vaccines for retaining an antigen in nasal cavity tissue and the transition thereof to the cerebral nervous system.

FIG. 13 shows the results of gamma ray measurements in the brain (A), the olfactory bulb (B), the nasal tissue (C), the nasal-associated lymphoid tissue (NALT) (D), the cervical lymph node (E), and the spleen (F).

As shown in FIG. 13, mucosal vaccines using nanogels remained, particularly in the nasal tissue (C), for a long period of time, although migration to the brain or the olfactory bulb was not observed. The results demonstrate that transnasal administration of the mucosal vaccines comprising cationic nanogels of the present invention yields the higher effects of antigen retention in the nasal cavity, compared with a case in which a mucosal vaccine is administered alone. In addition, the results demonstrate that such mucosal vaccines can be used as preparations for intranasal administration with excellent safety and effectiveness, and they do not migrate to the central nervous system as some adjuvants would.

All publications, patents, and patent applications cited herein are incorporated herein by reference in their entirety.

The invention claimed is:

1. A method for inducing an immune response in an animal comprising transmucosally administering to the animal an immunogenic preparation comprising a composite comprising an antigen and a nanogel, wherein the nanogel comprises a hydrophilic polysaccharide having a cationic functional group, wherein a hydrophobic cholesterol is added to the hydrophilic polysaccharide as a side chain.

2. The method of claim 1, wherein the cationic functional group is an amino group.

3. The method of claim 1, wherein the nanogel is cholesterol-bearing pullulan.

4. The method of claim 1, wherein the antigen is derived from a microorganism.

5. The method of claim 4, wherein the microorganism is selected from the group consisting of a virus, a bacterium, a protozoan, and a fungus.

6. The method of claim 5, wherein the virus antigen is selected from the group consisting of a C-terminal avirulent region of the heavy chain of botulinus toxin, tetanus toxoid, and AIDS virus membrane antigen molecule gag p24.

7. The method of claim 1, wherein the antigen is combined with the nanogel at a molar ratio of 1:1 to 1:10.

* * * * *